(12) United States Patent
Fitzgerald

(10) Patent No.: US 7,250,039 B2
(45) Date of Patent: Jul. 31, 2007

(54) COMPRESSION BULB HYPODERMIC SYRINGE

(75) Inventor: Lisa M. Fitzgerald, Sarasota, FL (US)

(73) Assignee: P. Rowan Smith, Jr., Houston, TX (US)

( * ) Notice: Subject to any disclaimer, the term of this patent is extended or adjusted under 35 U.S.C. 154(b) by 262 days.

(21) Appl. No.: 10/891,783

(22) Filed: Jul. 15, 2004

(65) Prior Publication Data

US 2006/0084926 A1    Apr. 20, 2006

(51) Int. Cl.
A61M 5/178    (2006.01)

(52) U.S. Cl. .................. 604/212; 604/192; 604/217

(58) Field of Classification Search ............. 604/192, 604/37, 142, 212, 217, 214; 128/200.22, 128/203.28; 401/185
See application file for complete search history.

(56) References Cited

U.S. PATENT DOCUMENTS

| | | | | |
|---|---|---|---|---|
| 465,161 A | * | 12/1891 | Chase | 604/77 |
| 3,452,757 A | * | 7/1969 | Ames | 604/8 |
| 3,570,626 A | * | 3/1971 | Mochida et al. | 181/164 |
| 3,991,757 A | * | 11/1976 | van Leer | 604/212 |
| 4,581,021 A | * | 4/1986 | Landau et al. | 604/214 |
| 4,674,655 A | * | 6/1987 | Lofgrer et al. | 222/48 |
| 4,692,157 A | * | 9/1987 | Landau et al. | 604/214 |
| 4,880,409 A | * | 11/1989 | Bergkvist et al. | 604/73 |
| 5,328,477 A | * | 7/1994 | Sitko | 604/134 |
| 5,337,925 A | * | 8/1994 | Ferrara, Jr. | 222/214 |
| 5,662,617 A | * | 9/1997 | Odell et al. | 604/192 |
| 6,156,012 A | * | 12/2000 | Nathan | 604/192 |
| 2001/0031947 A1 | * | 10/2001 | Heruth | 604/142 |

* cited by examiner

Primary Examiner—Nicholas D. Lucchesi
Assistant Examiner—Melissa A. McCorkle
(74) Attorney, Agent, or Firm—Richard L. Moseley

(57) ABSTRACT

A compression hypodermic syringe is disclosed wherein two leaves are hinged together. One leaf contains a receptacle for a collapsible capsule which contains a pre-measured dose of medication. The second leaf has a structure that acts as a plunger when the second leaf is folded over the first leaf. A double ended hypodermic needle is provided that has one end that pierces a membrane on the collapsible capsule and a second end that is exposed for insertion into a patient when the two leaves are folded together.

6 Claims, 8 Drawing Sheets

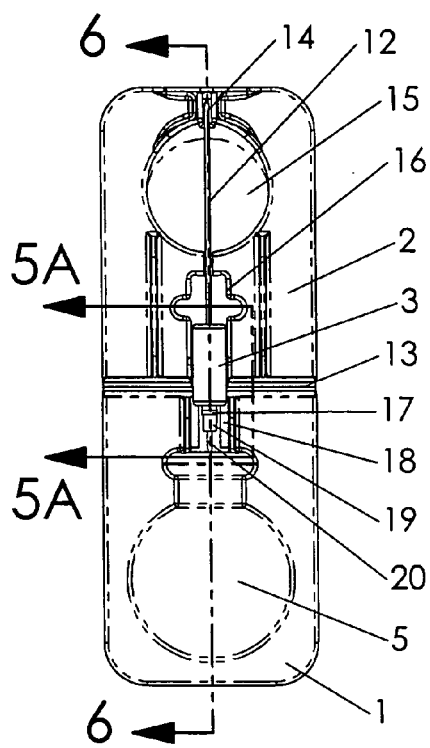
Figure 5
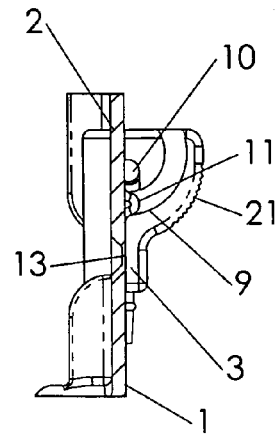
Figure 5A
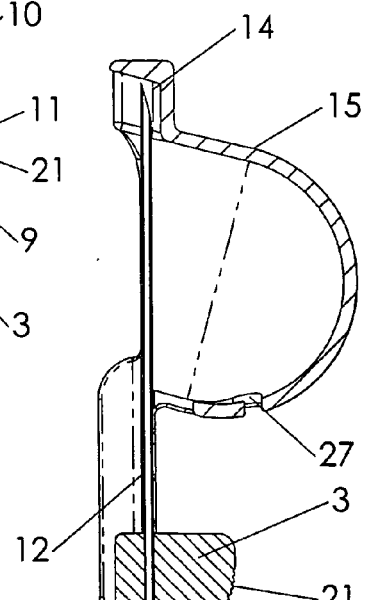
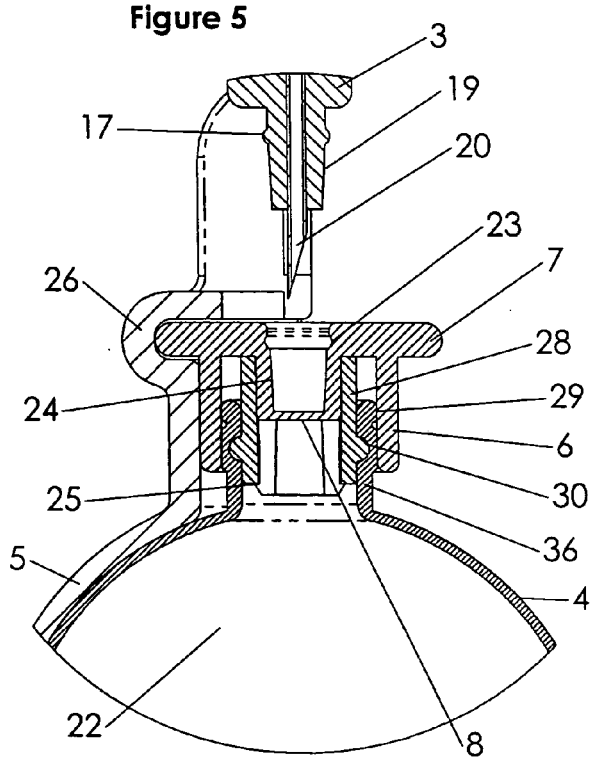
Figure 6A
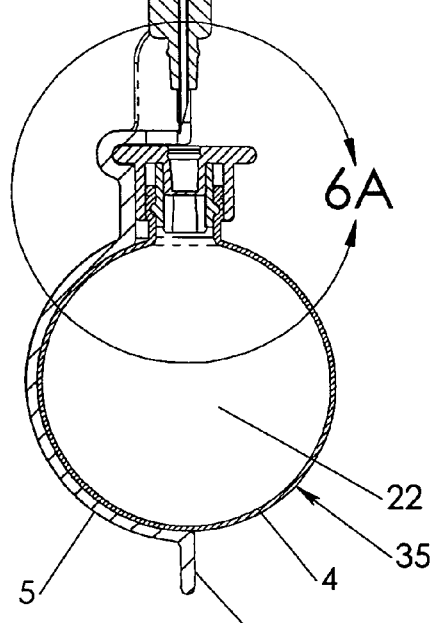
Figure 6

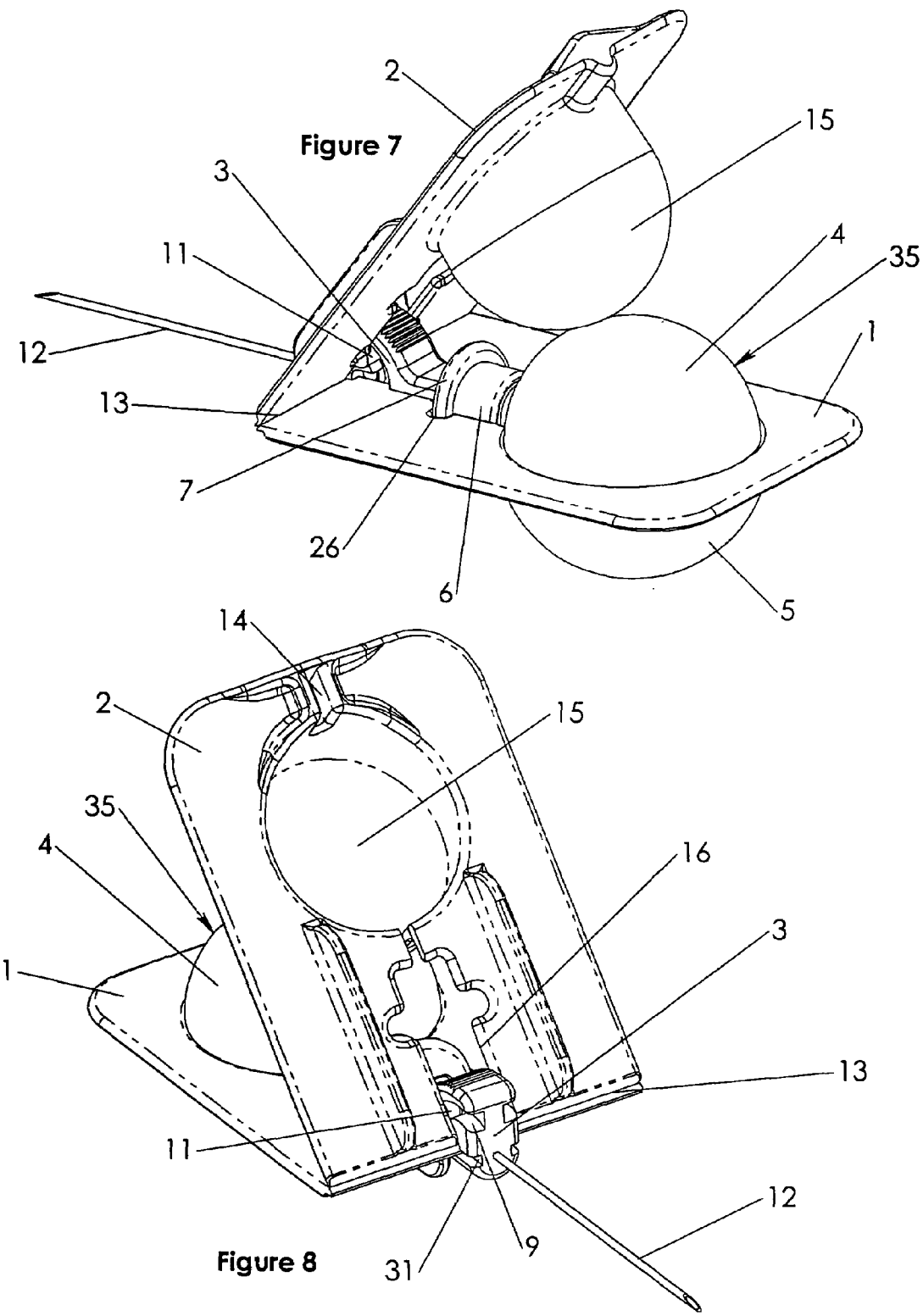

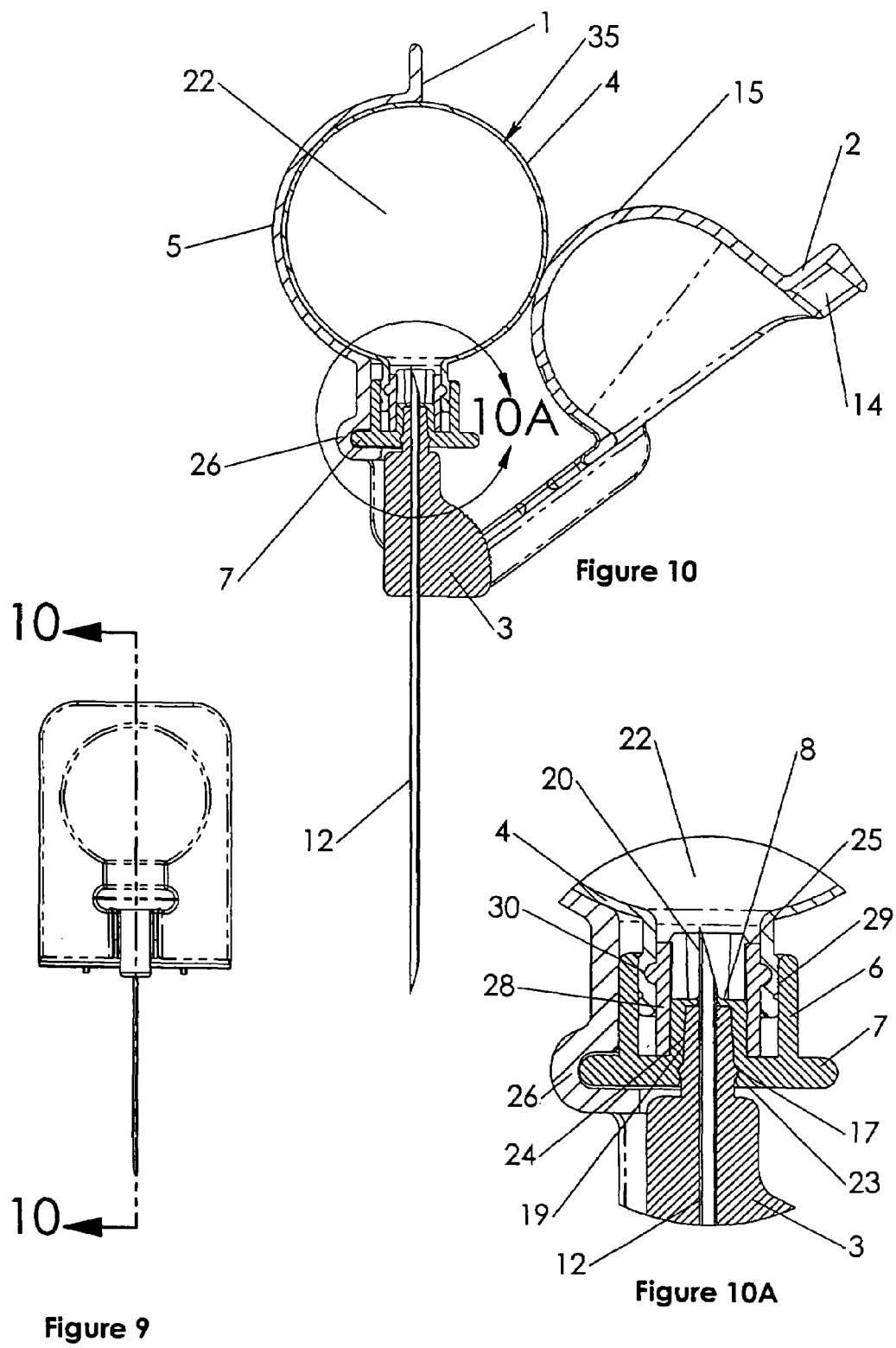

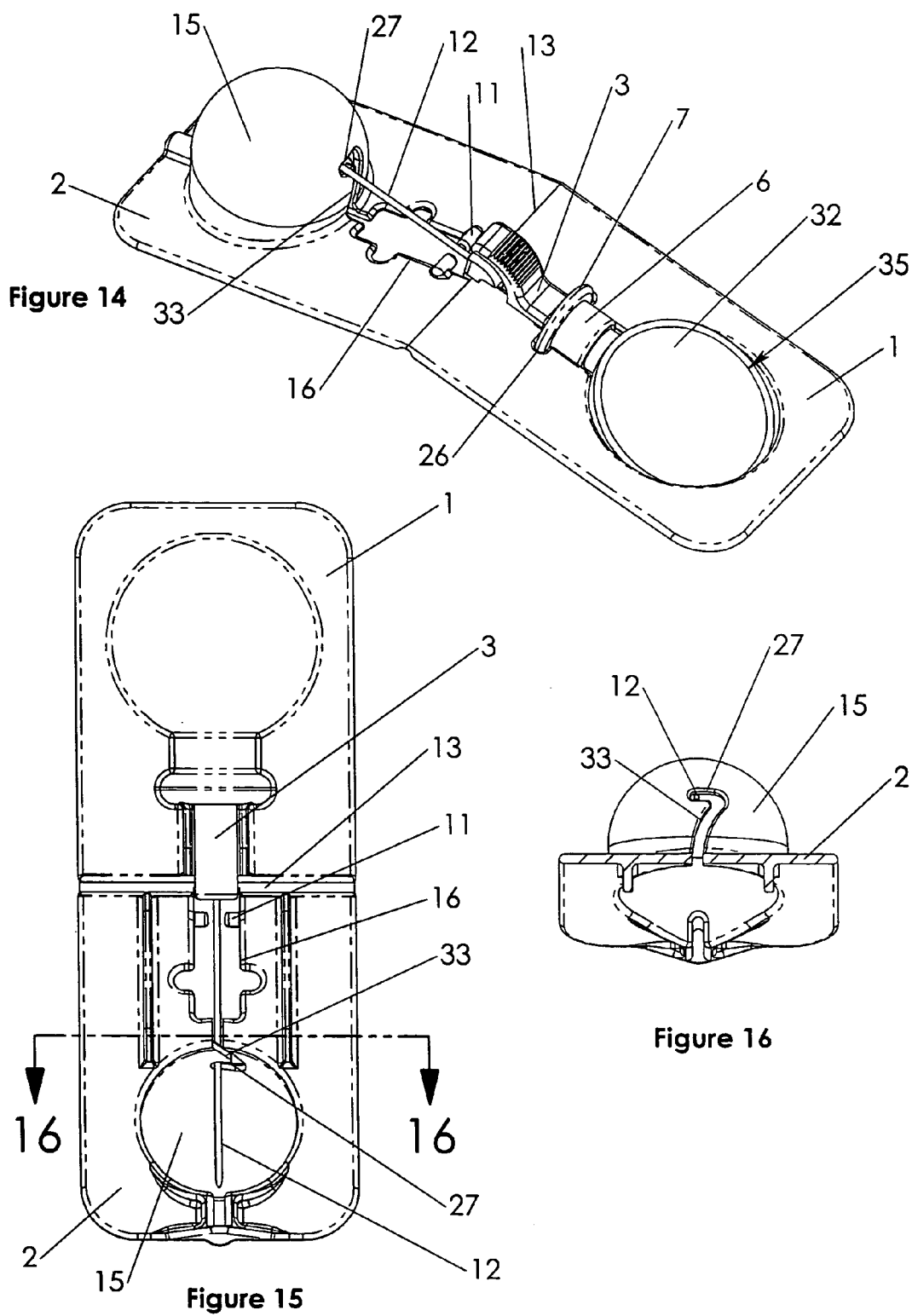

COMPRESSION BULB HYPODERMIC SYRINGE

BACKGROUND OF THE INVENTION

1. Field of the Invention

The present invention relates to a compact hypodermic syringe for injecting a pre-measured dose under adverse conditions. More particularly, the invention relates to a syringe wherein the doses are pre-loaded compressible capsules having the opening sealed by adhesive label. More particularly, the syringe is a foldable fully disposable device which after use is folded to enclose the hypodermic syringe safely.

2. Related Art

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick", or the accidental pricking of the person giving the injection after the syringe has been used.

Some of the recently patented retractable needle syringes include U.S. Pat. No. 4,692,156 (Haller); U.S. Pat. No. 4,675,005 (DeLuccia); U.S. Pat. No. 4,747,830 (Gloyer, et al); U.S. Pat. Nos. 4,790,822 and 4,950,251. All of the syringes disclosed include a hypodermic needle mounted on a carrier which is slidable in the barrel. The plunger is locked to this carrier after the injection has been given and is withdrawn up into the barrel by withdrawal of the plunger. The simplest mechanism for locking the plunger to the carrier is disclosed as a projection on the lower end of the plunger which engages through an opening in the upper end of the carrier.

One disadvantage of the above syringes is that the locking mechanism takes up some space in the barrel of the syringe and may prevent all of the measured liquid from being ejected by the plunger. This problem is exacerbated in the very small syringes such as the 1 cc tuberculin type. The liquid left in the barrel may be a substantial portion of the measured dose. In addition the narrowness of the barrel of the 1 cc syringe makes it difficult to design a needle carrier and locking mechanism that will fit in the barrel without enlarging the diameter so much as to make the calibration useless.

Venturini in U.S. Pat. No. 5,112,316 discloses a syringe similar to the retractable needle syringes described above except Venturini adds a spring outside the upper end of the syringe between the finger flange on the top of the barrel and the bottom surface of a projection at the top of the plunger to retract the plunger into the barrel after it has been locked onto the needle carrier. Venturini suffers the same drawbacks because the plunger must still be locked to the needle carrier.

Also there is a need for a simple, easy to use syringe for injecting pre-measured doses of medicines. While this need has been met by syringes having the medications pre-loaded, there is still a need where the user would like to select the medicine to be injected and utilize a syringe not pre-loaded.

SUMMARY OF THE INVENTION

The present invention provides a simple, easy to use syringe which may be used under difficult circumstances. The compression bulb hypodermic syringe allows an intra-muscular injection of a measured dose of antidote against a biological or chemical agent, or the injection of medications. The simplicity of design and ease of use make the device field-adaptable for emergency, war or third-world situations. The medications are pre-loaded in a compressible capsule whose hypodermic interface is sealed from contamination by an adhesive label which creates a double seal. The label, having markings as to the contents, is peeled away before loading into the syringe. This allows the medications to be transported contamination-free to the application site in extremely dirty environments. The compressible capsule is a drop in component that can quickly and simply loaded into the syringe applicator.

The syringe applicator features a two-piece design comprising a needle carrier assembly and an applicator body, each molded from a single piece of plastic. The needle carrier partially encloses a double-ended hypodermic needle. The applicator is folded on a living hinge that first causes the needle carrier to move until one end of the hypodermic needle punctures the capsule seal and communicates with the medication therein. Continuing to fold the applicator compresses the capsule, thereby ejecting the medication through the opposite end of the hypodermic needle into the patient.

When the applicator is folded in the opposite direction completely the exposed end of the hypodermic needle is contained safely within the applicator. The invention may be thus shown to comprise:

(a) a first leaf having a receptacle for a collapsible container, said first leaf defining an applicator holding body:

(b) a second leaf defining a plunger holding body which is hinged and connected to said first leaf and having a plunger which substantially conforms in size and shape as the collapsible container and mounted on said second leaf such that said plunger can engage a collapsible container in said enclosure when said second leaf is folded over said first leaf in one direction;

(c) a double-ended hypodermic needle having a first end for insertion into a patient and a second end which can puncture the closure on a collapsible container within said receptacle;

(d) said first end being exposed and said second end puncturing said collapsible container when said second leaf is folded part way over said first leaf in the direction of (b); and (e) said plunger being capable of collapsing a collapsible container contained within said receptacle when said second leaf is pressed firmly against said first leaf.

BRIEF DESCRIPTION OF THE DRAWING

FIG. 5 is a bottom view of the device as shown in FIG. 1.

FIG. 5A is a side elevational view taken along line 5A—5A of FIG. 5.

FIG. 6 is a side plan view in cross section of the opposite side as that of FIG. 3.

FIG. 6A is an enlarged cross sectional view of the area circled in FIG. 6.

FIG. 7 is a back perspective view of the device with the applicator folded and the device ready for use.

FIG. 8 is a front perspective view taken from the opposite angle as that of FIG. 7.

FIG. 9 is bottom of the device as shown in FIGS. 7 and 8.

FIG. 10 is a side plan view in cross section taken along line 10—10 in FIG. 9.

FIG. 10A is a detailed view of the area circled in FIG. 10.

FIG. 14 is a top perspective view of the device being refolded.

FIG. 15 is a top view of the device completely refolded 180° from the injection position.

FIG. 16 is an end view taken along line 16—16 of FIG. 16.

DESCRIPTION OF THE PREFERRED EMBODIMENTS

Figure 1:
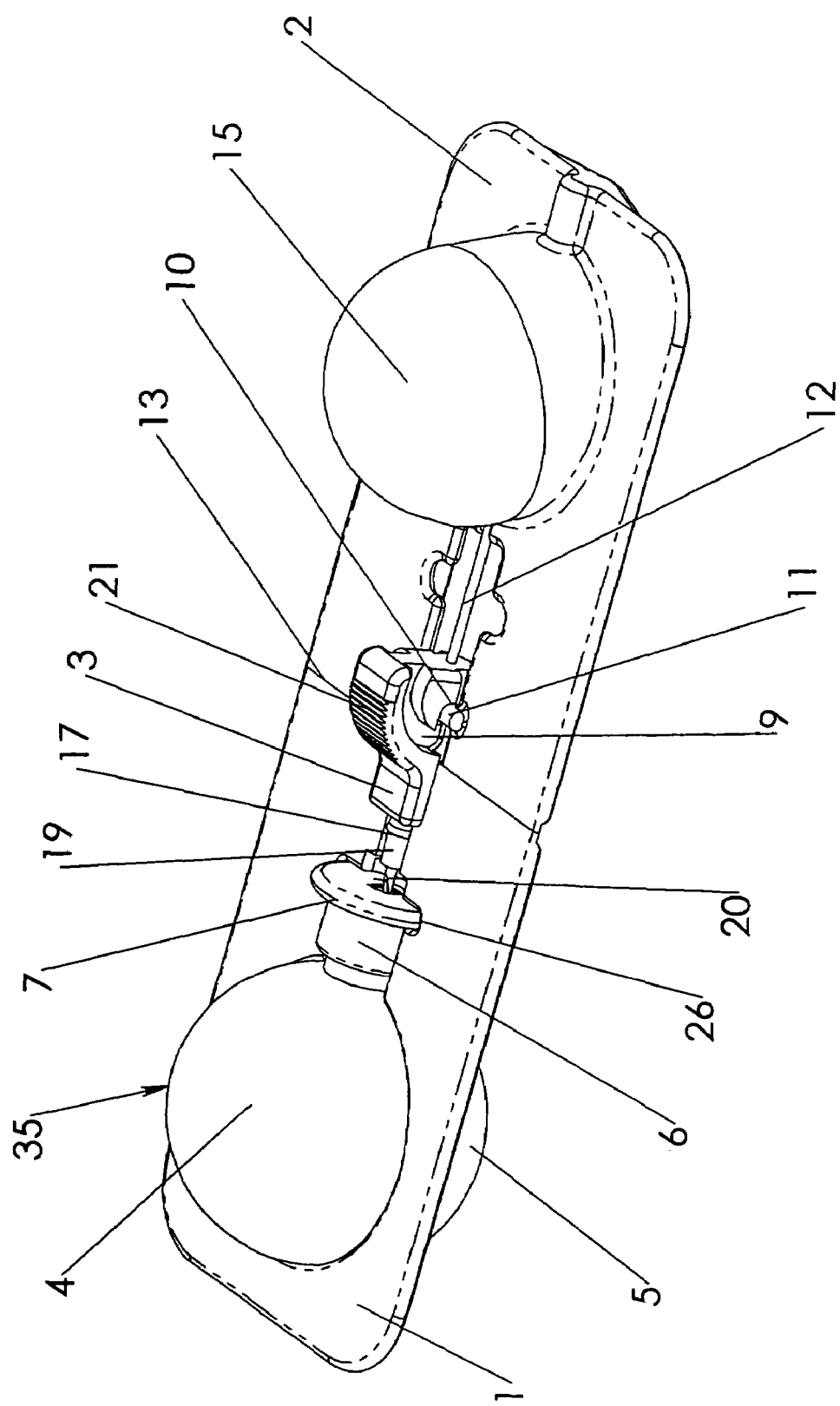
FIG. 1 is a top perspective view of the device in the initial state with a compressible capsule loaded.

For a detailed description of the preferred embodiment the reader is referred to the appended figures in which like components are given like numerals for ease of reference.

For quick reference all of the reference numerals are listed in Table I below and their corresponding parts identified with the figures in which the parts are identified. The parts may be shown in other figures but are identified by the reference numerals in the listed figures only.

Table 1

TABLE I

| No. | Description | FIG. Number |
|---|---|---|
| 1 | Applicator holding body | 1–3, 4–5, 5A, 6, 7–8, 10, 12–15, 17 |
| 2 | Applicator plunger body | 1–3, 4–5, 5A, 7–8, 10, 13–17 |
| 3 | Needle carrier | 1–3, 4–5, 5A, 6, 6A, 7–8, 10, 10A, 12, 15, 17 |
| 4 | Vessel | 1–3, 4, 6, 6A, 7–8, 10, 10A, 12, 118 |
| 5 | Capsule holding cavity | 1, 3, 5, 6, 6A, 7, 10, 12–13, 18 |
| 6 | Capsule closure | 1–3, 6A, 7, 10A, 12–14, 17–18 |
| 7 | Capsule retaining ring | 1–3, 6A, 7, 10A, 12–14, 17 |
| 8 | Membrane | 5, 6A, 10A, 12, |
| 9 | Driving track | 1, 3, 5A, 8, 13, 17 |
| 10 | Applicator locking slot | 1, 3, 3A, 5A |
| 11 | Actuator pin | 1–3, 3A, 4, 5A, 7–8, 13–15, 17 |
| 12 | Hypodermic needle | 1–2, 4, 5, 6, 1–8, 10, 10A, 12–17 |
| 13 | Living hinge | 1–3, 5, 5A, 7–8, 13–15, 17 |
| 14 | Needle safety cavity | 3, 5, 6, 8, 12–13 |
| 15 | Plunger | 1–3, 4–6, 7–8, 10, 12–17 |
| 16 | Carrier aperture | 2, 5, 8, 14–15, 17 |
| 17 | Carrier retainer ring | 1–3, 5, 6A, 10A, 12 |
| 18 | Carrier sliding track | 4, 5, 17 |
| 19 | Carrier luer seal body | 1–3, 5, 6A, 10A, 12, 17 |
| 20 | Piercing needle | 1, 5, 6A, 10A, 12, 17 |
| 21 | Finger push interface | 1, 4, 5A, 6, 17 |
| 22 | Capsule inner cavity | 6, 6A, 10, 10A, 12 |
| 23 | Carrier locking notch | 6A, 10A |
| 24 | Capsule luer seal cavity | 6A, 10A, 12 |
| 25 | Capsule closure retainer latch | 6A, 10A, 12 |
| 26 | Capsule retaining slot ring | 1, 6A, 7, 10, 10A, 12, 14, 17 |
| 27 | Safety slot | 4, 6, 14–16 |
| 28 | Capsule closure inner ring | 6A, 10A, 12 |

TABLE I-continued

| No. | Description | FIG. Number |
|---|---|---|
| 29 | Capsule closure inner wall | 6A, 10A, 12 |
| 30 | Capsule sealing ring | 6A, 10A, 12 |
| 31 | Carrier track slot | 4, 8, 13, 17 |
| 32 | Capsule compressed | 12 |
| 33 | Deflecting surface | 16 |
| 34 | Sealing label | 18 |
| 35 | Capsule assembly | 1, 3, 6–8, 10, 12, 14, 17, 18 |
| 36 | Vessel neck | 6A |
| 37 | Locking slot detent | 3, 3A |

Figure 2:
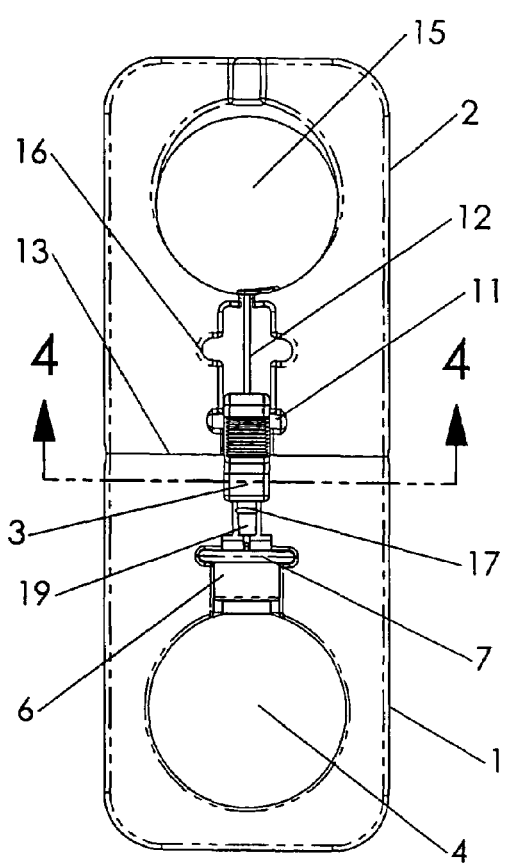
FIG. 2 is a top view of the device as shown in FIG. 1.
Figure 3:
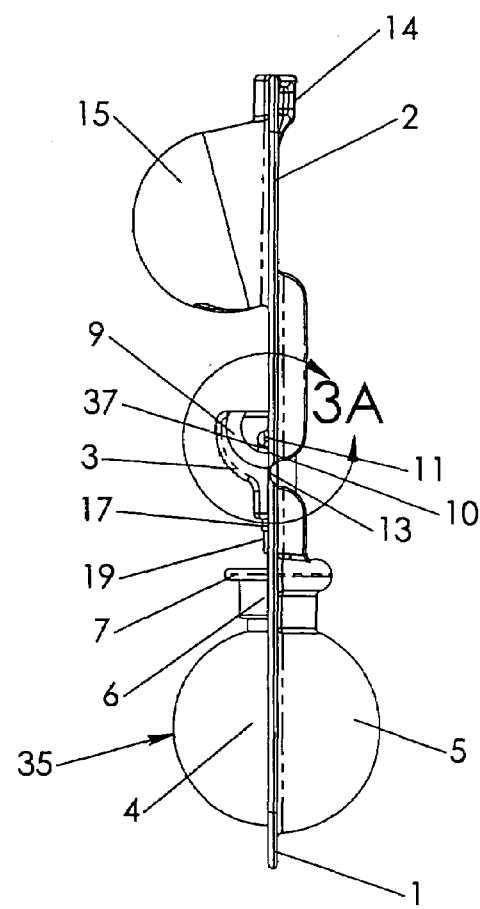
FIG. 3 is a side plan view of the device as shown in FIG. 1.
Figure 4:
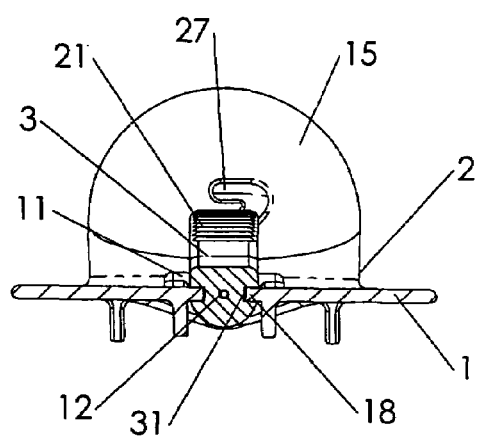
FIG. 4 is an end view in partial cross section taken along lines 4—4 of FIG. 2.
Figure 3A:
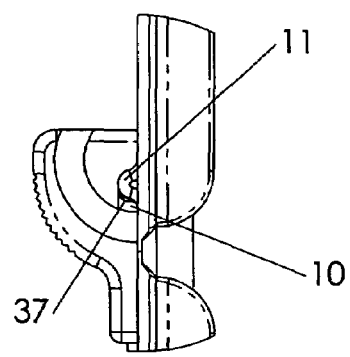
FIG. 3A is a detailed view of the area circled in FIG. 3.
Figure 11:
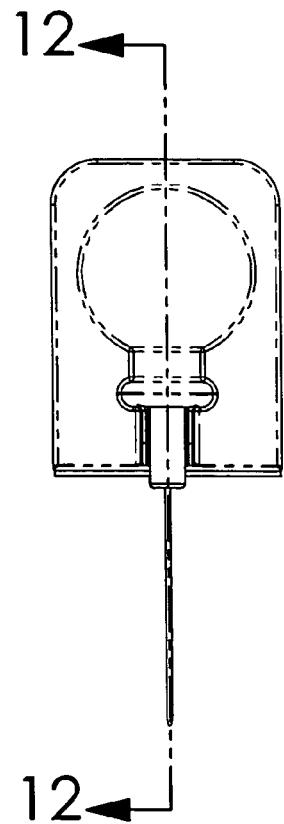
FIG. 11 is a bottom view of the device after the plunger has compressed the capsule.
Figure 12:
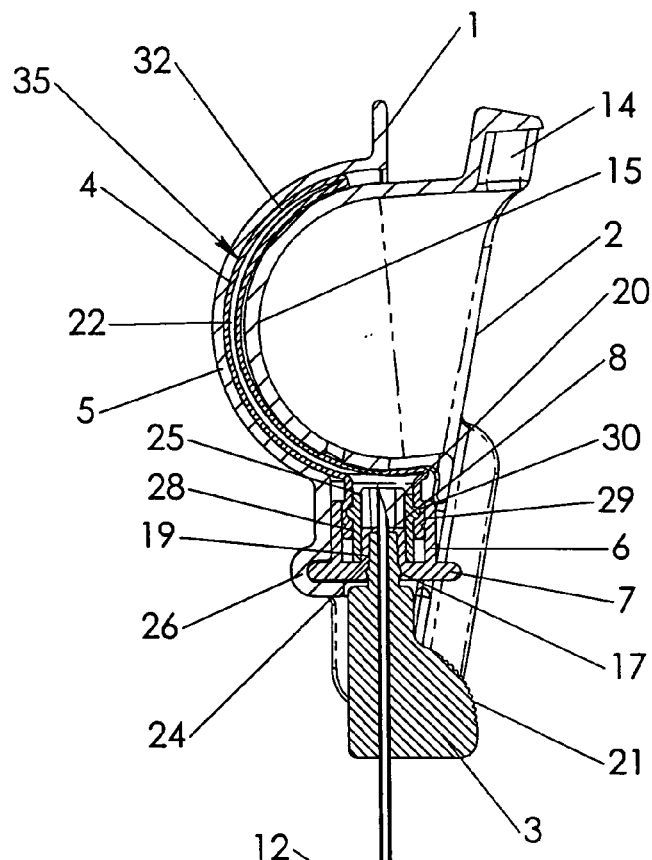
FIG. 12 is a side plan view in cross section taken along the line 12—12 in FIG. 11.
Figure 13:
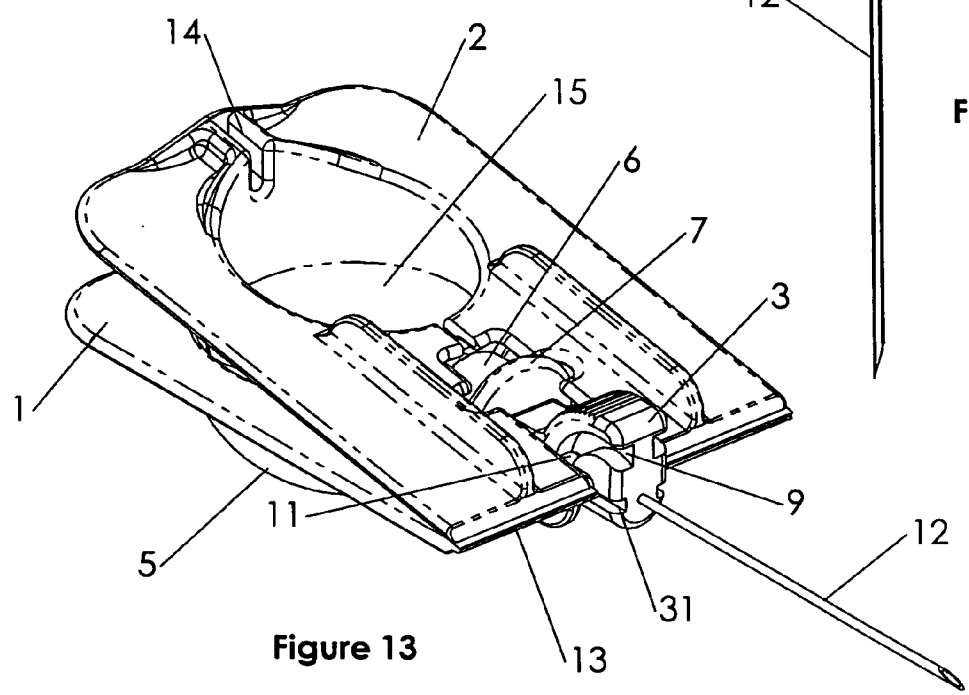
FIG. 13 is a front perspective view with after the plunger has compressed the capsule.

Referring first to FIGS. 1 and 2, the device is shown in its initial state with the applicator holding body 1 and the applicator plunger body 2 are molded as one plastic part along with and connected by a flexible living hinge 13. The two bodies are in the form of rectangular leaves or slabs. In FIG. 4 the needle carrier 3 is seen to be captured laterally and vertically by a carrier track slot 31 contacting the carrier sliding track 18. FIG. 3 shows that actuator pin 11 is captured by applicator locking slot 10 on the needle carrier 3 preventing any angular motion around the pivot point defined by the living hinge 13. Locking slot detent 37, located in the applicator locking slot 10, allows a light snap fit between actuator pin 11 and the needle carrier 3 to temporarily retain the needle carrier 3 in this locked position. The distal end of the hypodermic needle 12 is safely stowed in the needle safety cavity 14.

Figure 18:
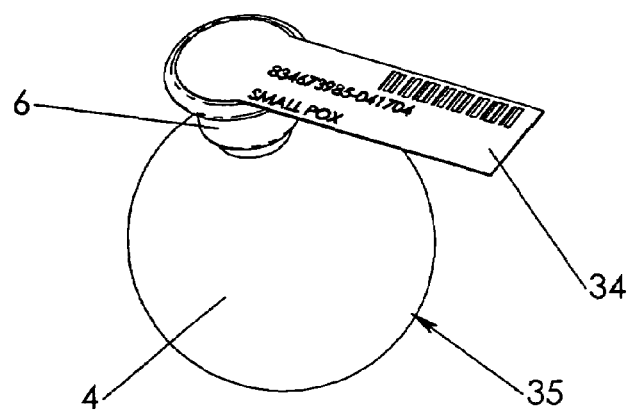
FIG. 18 is a perspective view of the collapsible capsule assembly as used in the present invention.

Referring now to FIGS. 1, 6A and 18, capsule assembly 35 comprising collapsible vessel or container 4, capsule closure 6 and capsule closure inner ring 28, is positioned in the applicator holding body 1. This capsule assembly contains a pre-loaded medication dose in the capsule inner cavity 22. The inner cavity 22 is sealed by compressing the vessel neck 36 between the capsule closure wall 29 and the capsule sealing ring 30 located on the capsule closure inner ring 28. This seal is retained by the capsule closure retainer latch 25 snapping into the capsule closure inner ring 28. The inner cavity 22 is also sealed by membrane 8 located in the capsule closure 6. The sealing label 34, as shown on FIG. 18, seals the capsule luer seal cavity 24 and the membrane 8 from contaminants. The capsule assembly 35 is positioned by capsule holding cavity 5. Due to the elastic properties of the vessel 4, an additional retainer comprising capsule retaining ring slot 26 on applicator holding body 1 and capsule retaining ring 7, part of the capsule closure 6, is required to hold the capsule assembly 35 stable.

Operation

Figure 17:
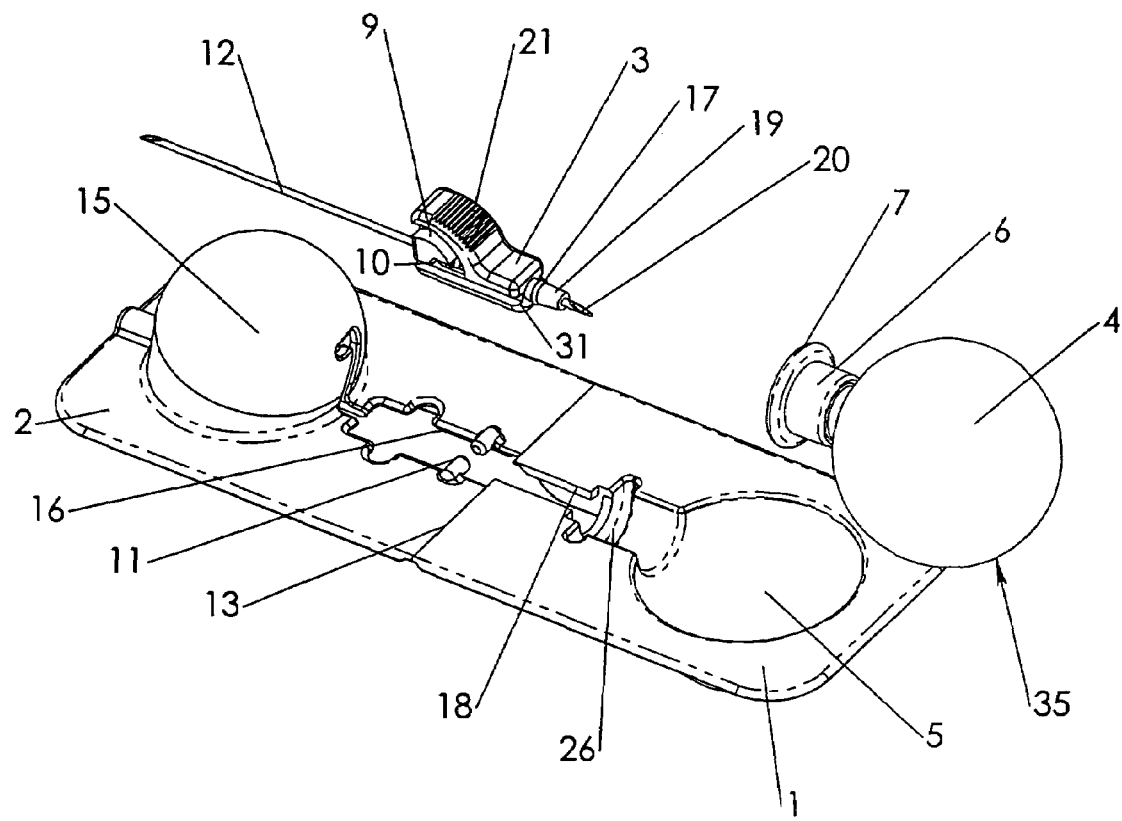
FIG. 17 is an exploded view of the syringe of the present invention.

Referring to FIGS. 5 and 5A, needle carrier is pushed by means of finger push interface 21 to a position where the actuator pin 11 is in the driving track 9. This allows angular movement of living hinge 13 between applicator holding body 1 and applicator plunger body 2. As seen in FIG. 17, the plastic needle carrier 3 is molded around the hypodermic needle 12 creating piercing needle 20 at the proximal end and hypodermic needle 12 at the distal end. Hypodermic needle 12 is thus a double ended canula and sharp at both ends.

As seen in FIGS. 7 and 8, folding the applicator plunger body 2 along living hinge 13 toward the applicator holding body 1 drives actuator pin 11 towards the distal end of the applicator holding body 1 in a circular motion as defined by a pivot point along the axis of living hinge 13. This motion is translated to the needle carrier 3 by means of the driving track 9. The needle carrier 3 travels through the carrier aperture 16 and along sliding track 18, captured by carrier track slot 31, until the circular driving track 9 axis becomes coincident with the axis of the living hinge 13. At this point the actuator pin 11 travels concentric to the circular driving track 9 and further lateral movement of the needle carrier 3 is stopped.

At this point, as seen in FIG. 10A, the needle carrier 3 has pushed needle 20 through membrane 8 in the capsule closure 6 allowing medication to flow through to hypodermic needle 12. Also, carrier retainer ring 17 has permanently snapped into carrier locking notch 23 and carrier luer seal body 19 on the needle carrier 3 has seated into capsule luer seal cavity 24 to form a luer seal.

In the injection phase, further folding of the applicator plunger towards the applicator holding body 1 as shown in FIGS. 7 and 8 causes the plunger 15 to contact the vessel 4. The vessel 4 is made from a pliable elastomer and is collapsed by the plunger 15 which is shaped to substantially conform to the vessel. The vessel collapses, reducing the volume of the inner cavity 22 thereby pushing the contents of the vessel through hypodermic needle 12.

Referring now to FIGS. 14–16, storage of the needle is shown after injecting the medication. The needle 12 is stowed in a safe position inside plunger 15 by folding the applicator body 2 180° allowing the hypodermic needle 12 to pass through the carrier aperture 16 and into the safety slot 27. Continuing to fold causes the hypodermic needle 12 to be sprung to one side by deflecting surface 33 and then captured by snapping back to its normal position in the top of the safety slot 27.

The foregoing description of the invention has been directed to a particular preferred embodiment of the present invention for the purposes of explanation and illustration. It will be apparent to those skilled in the art that many modifications and changes in the apparatus may be made without departing from the scope and spirit of the invention. It is therefore intended that the following claims cover all equivalent modifications and variations as fall within the scope of the invention as defined by the claims.

The invention claimed is:

1. A syringe for injecting fluids from a container having a pre-measured dose of fluid comprising:
    (a) a first flat leaf having a receptacle for a collapsible capsule;
    (b) a needle carrier slideably mounted in a carrier track on said first flat leaf and having an arcuate driving track integrated therein;
    (c) a second flat leaf hingedly connected to said first leaf having an actuator pin mounted on the surface engageable with said arcuate driving track to move said needle carrier along said carrier track when said second leaf is folded over said first leaf in one direction;
    (d) a double ended hypodermic needle mounted in said needle carrier and having a first end for insertion into a patient and a second end which can puncture the closure on a collapsible capsule within said receptacle when said second leaf is folded over said first leaf in one direction; and
    (e) a plunger mounted on said second flat leaf that substantially conforms in shape to said receptale said plunger being capable of collapsing a collapsible capsule contained within said receptacle when said second leaf is pressed firmly against said first leaf.

2. The syringe according to claim 1 wherein said first end is safely enclosed between said first and second leaves when said first and second leaves are folded in a second direction which is the reverse direction of said first direction.

3. The syringe according to claim 1 further comprising a collapsible capsule secured in said receptacle.

4. The syringe according to claim 3 wherein said collapsible capsule comprises a membrane which is piercable by said second end and a removable adhesive seal over said membrane, said removable adhesive seal being removed before said collapsible capsule is placed into said receptacle.

5. The syringe according to claim 3 wherein said receptacle has the shape of substantially one-half the profile of said collapsible capsule.

6. A syringe for injecting fluids from a container having a pre-measured dose of fluid comprising:
    (a) a first flat leaf having a receptacle for a collapsible capsule:
    (b) a collapsible capsule containing a pre-measure dose of medication disposed within said receptacle and comprising a piercable membrane seal;
    (c) a needle carrier slideably mounted in a carrier track on said first flat leaf receptacle and having an arcuate driving track integrated therein;
    (d) a second leaf hingedly connected to said first leaf having an actuator pin mounted on the surface engageable with said arcuate driving track to move said needle carrier along said carrier track when said second leaf is folded over said first leaf in a first direction;
    (e) a double-ended hypodermic needle mounted in said needle carrier and having a first end for insertion into a patient and a second end for puncturing said membrane on said collapsible capsule within said receptacle when said second leaf is folded over said first leaf in one direction;
    (f) said first end being exposed and said second end puncturing said collapsible capsule when said second leaf is folded part way over said first leaf in said first direction; and
    (g) a plunger being capable of collapsing said collapsible capsule contained within said receptacle when said second leaf is pressed firmly against said first leaf.

* * * * *